United States Patent
Arora et al.

(10) Patent No.: US 12,307,666 B2
(45) Date of Patent: May 20, 2025

(54) SYSTEMS AND METHODS FOR PREDICTING POST-OPERATIVE RIGHT VENTRICULAR FAILURE USING ECHOCARDIOGRAMS

(71) Applicant: The Board of Trustees of the Leland Stanford Junior University, Stanford, CA (US)

(72) Inventors: Rohan Shad Arora, Stanford, CA (US); William Hiesinger, Stanford, CA (US); Nicolas Tung-Da Quach, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 427 days.

(21) Appl. No.: 17/997,468

(22) PCT Filed: Apr. 26, 2021

(86) PCT No.: PCT/US2021/029168
§ 371 (c)(1),
(2) Date: Oct. 28, 2022

(87) PCT Pub. No.: WO2021/222106
PCT Pub. Date: Nov. 4, 2021

(65) Prior Publication Data
US 2023/0169651 A1    Jun. 1, 2023

Related U.S. Application Data

(60) Provisional application No. 63/018,270, filed on Apr. 30, 2020.

(51) Int. Cl.
*G06T 7/00* (2017.01)
*G06N 3/045* (2023.01)
(Continued)

(52) U.S. Cl.
CPC .......... *G06T 7/0012* (2013.01); *G06N 3/045* (2023.01); *G06N 3/0464* (2023.01); *G06N 3/048* (2023.01);
(Continued)

(58) Field of Classification Search
CPC .................. G06T 7/0012; G06T 7/246; G06T 2207/10016; G06T 2207/10132;
(Continued)

(56) References Cited

U.S. PATENT DOCUMENTS

2011/0190631 A1* 8/2011 Kramer .............. A61N 1/36514
600/443
2017/0232166 A1* 8/2017 Potenziano .......... A61M 60/20
600/17

(Continued)

FOREIGN PATENT DOCUMENTS

| WO | 2019016156 A1 | 1/2019 |
| WO | 2019178404 A1 | 9/2019 |
| WO | 2021222106 A1 | 11/2021 |

OTHER PUBLICATIONS

International Preliminary Report on Patentability for International Application PCT/US2021/029168, Report issued Oct. 27, 2022, Mailed on Nov. 10, 2022, 5 pgs.
(Continued)

*Primary Examiner* — Van D Huynh
(74) *Attorney, Agent, or Firm* — KPPB LLP (57) ABSTRACT

Systems and methods for incorporating machine learning to predict post operative right ventricular failure using echocardiograms are described. In an embodiment, the system obtains echocardiography video data describing a patient's heart, generates several dense trajectory descriptors based on the echocardiography video data, reduces the dense trajectory descriptors to a bag-of-words representation, gen-
(Continued)

erates a first prediction metric of RV failure based on the bag-of-words representation, generates a second prediction metric based on the echocardiography video data using a neural network, and generates an output prediction metric by applying a weighted classifier to the first prediction metric and the second prediction metric.

12 Claims, 7 Drawing Sheets
(5 of 7 Drawing Sheet(s) Filed in Color)

(51) Int. Cl.

| | |
|---|---|
| *G06N 3/0464* | (2023.01) |
| *G06N 3/048* | (2023.01) |
| *G06N 3/08* | (2023.01) |
| *G06T 7/246* | (2017.01) |
| *G16H 50/30* | (2018.01) |

(52) U.S. Cl.
CPC ............... *G06N 3/08* (2013.01); *G06T 7/246* (2017.01); *G16H 50/30* (2018.01); *G06T 2207/10016* (2013.01); *G06T 2207/10132* (2013.01); *G06T 2207/20081* (2013.01); *G06T 2207/20084* (2013.01); *G06T 2207/30048* (2013.01); *G06T 2207/30241* (2013.01)

(58) Field of Classification Search
CPC . G06T 2207/20081; G06T 2207/20084; G06T 2207/30048; G06T 2207/30241; G06N 3/045; G06N 3/0464; G06N 3/048; G06N 3/08; G06N 3/084; G06N 20/10; G16H 50/30; G16H 50/70; A61B 8/0883; A61B 8/5223

See application file for complete search history.

(56) References Cited

U.S. PATENT DOCUMENTS

| | | | | |
|---|---|---|---|---|
| 2018/0119222 | A1* | 5/2018 | Zou | C12Q 1/6883 |
| 2020/0174020 | A1* | 6/2020 | Steinhoff | G01N 33/5094 |
| 2020/0226757 | A1* | 7/2020 | Hare, II | G16H 40/63 |
| 2021/0000449 | A1* | 1/2021 | Deo | A61B 5/7267 |
| 2021/0150693 | A1* | 5/2021 | Fornwalt | G06N 3/045 |
| 2021/0287367 | A1* | 9/2021 | Meyer | G06T 7/13 |
| 2024/0212143 | A1* | 6/2024 | Buckler | G06V 10/82 |

OTHER PUBLICATIONS

International Search Report and Written Opinion for International Application No. PCT/US2021/029168, Search completed Jul. 13, 2021, Mailed Aug. 12, 2021, 10 pgs.
"INTERMACS Adverse Event Definitions: Adult and Pediatric Patients", Appendix A: Adverse Event Definitions, STS Intermacs Database, Manual of Operations Version 5.0 (2016), obtained from http://www.uab.edu/medicine/intermacs/images/protocol_5.0/appendix_a/AE-Definitions-Final-02-4-2016.docx on Apr. 10, 2019.
Amsallem et al., "Right ventricular load adaptability metrics in patients undergoing left ventricular assist device implantation", The Journal of Thoracic and Cardiovascular Surgery, vol. 157, No. 3, Mar. 2019, pp. 1023-1033e1-e4, doi: 10.1016/j.jtcvs.2018.08.095.
Atluri et al., "Predicting Right Ventricular Failure in the Modern, Continuous Flow Left Ventricular Assist Device Era", The Annals of Thoracic Surgery, vol. 96, 2013, pp. 857-864, discussion pp. 863-864, doi: 10.1016/j.athoracsur.2013.03.099.
Attia et al., "An artificial intelligence-enabled ECG algorithm for the identification of patients with atrial fibrillation during sinus rhythm: a retrospective analysis of outcome prediction", Lancet, vol. 394, 2019, pp. 861-867, doi: 10.1016/S0140-6736(19)31721-0.
Aymami et al., "The Incremental Value of Right Ventricular Size and Strain in the Risk Assessment of Right Heart Failure Post—Left Ventricular Assist Device Implantation", Journal of Cardiac Failure, vol. 24, pp. 823-832, doi: 10.1016/j.cardfail.2018.10.012.
Bach et al., "On Pixel-Wise Explanations for Non-Linear Classifier Decisions by Layer-Wise Relevance Propagation", PLoS ONE, vol. 10, No. 7, Article e0130140, Jul. 10, 2015, pp. 1-46, doi: 10.1371/journal.pone.0130140.
Benjamin et al., "Heart Disease and Stroke Statistics—2017 Update: A Report from the American Heart Association", Circulation, vol. 135, 2017, pp. e146-e603, doi: 10.1161/CIR.0000000000000485. (Presented in 2 parts).
Dandel et al., "Load Dependency of Right Ventricular Performance is a Major Factor to be Considered in Decision Making Before Ventricular Assist Device Implantation", Circulation, vol. 128, Suppl 1, 2013, pp. S14-S23, doi: 10.1161/CIRCULATIONAHA. 112.000335.
Davis et al., "The Relationship Between Precision-recall and Roc Curves", Proceedings of the 23rd International Conference on Machine Learning, vol. 148, 2006, pp. 233-240, doi: 10.1145/1143844.1143874.
De Long et al., "Comparing the Areas Under Two or More Correlated Receiver Operating Characteristic Curves: A Nonparametric Approach", Biometrics, vol. 44, No. 3, Sep. 1998, pp. 837-845, doi: 10.2307/2531595.
Drakos et al., "Risk Factors Predictive of Right Ventricular Failure After Left Ventricular Assist Device Implantation.", The American Journal of Cardiology, vol. 105, 2010, pp. 1030-1035, doi: 10.1016/j.amjcard.2009.11.026.
Estrada et al., "Postoperative Right Ventricular Failure in Cardiac Surgery", Cardiology Research, vol. 7, No. 6, 2016, pp. 185-195, doi: 10.14740/cr500e.
Fawcett, "An introduction to ROC analysis", Pattern Recognition Letters, vol. 27, 2006, pp. 861-874, doi: 10.1016/j.patrec.2005.10.010.
Fitzpatrick et al., "Risk Score Derived from Pre-operative Data Analysis Predicts the Need for Biventricular Mechanical Circulatory Support", The Journal of Heart and Lung Transplantation, vol. 27, No. 12, 2008, pp. 1286-1292, doi: 10.1016/j.healun.2008.09.006.
Gerber et al., "Atherosclerotic Burden and Heart Failure After Myocardial Infarction", Journal of the American Medical Association Cardiology, vol. 1, 2016, pp. 156-162, doi: 10.1001/jamacardio.2016.0074.
Glorot et al., "Understanding the difficulty of training deep feedforward neural networks", Proceedings of the 13th International Conference on Artificial Intelligence and Statistics, (AISTATS) 2010, Chia Laguna Resort, Sardinia, Italy, vol. 9 of JMLR:W&CP 9, pp. 249-256.
Kalogeropoulos et al., "Validation of clinical scores for right ventricular failure prediction after implantation of continuous-flow left ventricular assist devices", The Journal of Heart and Lung Transplantation, vol. 34, No. 12, 2015, pp. 1595-1603, doi: 10.1016/j.healun.2015.05.005.
Kiernan et al., "Sharing the Care of Mechanical Circulatory Support: Collaborative Efforts of Patients/Caregivers, Shared-Care Sites, and Left Ventricular Assist Device Implanting Centers", Circulation: Heart failure, vol. 8, 2015, pp. 629-635, doi: 10.1161/CIRCHEARTFAILURE.114.001767.
Kingma et al., "Adam: A Method for Stochastic Optimization, International Conference on Learning Representations (ICLR)", 2015, arXiv:1412.6980v9 [cs.LG], Jan. 30, 2017, 15 pgs., doi: 10.48550/arXiv.1412.6980.
Kirklin et al., "Eighth annual INTERMACS report: special focus on framing the impact of adverse events", The Journal of Heart and Lung Transplantation, vol. 36, 2017, pp. 1080-1086, doi: 10.1016/j.healun.2017.07.005.
Konstam et al., "Evaluation and Management of Right-sided Heart Failure: A Scientific Statement from the American Heart Association", Circulation, vol. 137, 2018, pp. e578-e622, doi: 10.1161/CIR.0000000000000560.
Larue et al., "Clinical Outcomes Associated with INTERMACS Defined Right Heart Failure after Left Ventricular Assist Device (56) References Cited

OTHER PUBLICATIONS

Implantation.", The Journal of Heart and Lung Transplantation, vol. 36, No. 4, 2017, pp. 475-477, doi: 10.1016/j.healun.2016.12.017.
Lo et al., "Right ventricular failure after implantation of continuous flow left ventricular assist device: analysis of predictors and outcomes", Clinical Transplantation, vol. 29, 2015, pp. 763-770, doi: 10.1111/ctr.12577.
Loghmanpour et al., "A Bayesian Model to Predict Right Ventricular Failure Following Left Ventricular Assist Device Therapy", Journal of the American College of Cardiology: Heart Failure, vol. 4, No. 9, 2016, pp. 711-721, doi: 10.1016/j.jchf.2016.04.004.
Matthews et al., "The Right Ventricular Failure Risk Score: A Pre-Operative Tool for Assessing the Risk of Right Ventricular Failure in Left Ventricular Assist Device Candidates", Journal of the American College of Cardiology, vol. 51, No. 22, 2008, pp. 2163-2172, doi: 10.1016/j.jacc.2008.03.009.
McInnes et al., "UMAP: Uniform Manifold Approximation and Projection for Dimension Reduction", arXiv:1802.03426v3, Sep. 18, 2020, 63 pgs., https://doi.org/10.48550/arXiv.1802.03426.
McKinney et al., "International evaluation of an AI system for breast cancer screening", Nature, vol. 577, No. 7788, 2020, pp. 89-94, doi: 10.1038/s41586-019-1799-6.
Mehra et al., "A Fully Magnetically Levitated Circulatory Pump for Advanced Heart Failure", The New England Journal of Medicine, vol. 376, No. 5, 2017, pp. 440-450, doi: 10.1056/NEJMoa1610426.
Mehra et al., "Two-Year Outcomes with a Magnetically Levitated Cardiac Pump in Heart Failure", The New England Journal of Medicine, vol. 378, No. 15, 2018, pp. 1386-1395, doi: 10.1056/NEJMoa1800866.
Ouyang et al., "Video-based Ai for beat-to-beat assessment of cardiac function", Nature, vol. 580, No. 7802, 2020, pp. 252-256, doi: 10.1038/s41586-020-2145-8.
Rajpurkar et al., "AppendixNet: Deep Learning for Diagnosis of Appendicitis from a Small Dataset of CT Exams Using Video Pretraining", Scientific Reports, vol. 10, No. 3958, 2020, 7 pgs., doi: 10.1038/s41598-020-61055-6.
Rajpurkar et al., "Deep learning for chest radiograph diagnosis: a retrospective comparison of the cheXneXt algorithm to practicing radiologists", Public Library of Science Medicine, vol. 15, No. 11, 2018, e1002686, 17 pgs., doi: 10.1371/journal.pmed.1002686.
Robin et al., "pROC: an open-source package for R and S+ to analyze and compare ROC curves", BMC Bioinformatics, vol. 12, No. 77, 2011, 8 pgs., doi: 10.1186/1471-2105-12-77.
Shad et al., "A radiomics approach to artificial intelligence in echocardiography: Predicting post-operative right ventricular failure", May 11, 2020. [retrieved on Jul. 13, 2021]. Retrieved from the Internet: <URL: https://www.medrxiv.org/content/medrxiv/early/2020/05/11/2020.05.05.20092494.full.pdf>, pp. 1-9, doi: 10.1101/2020.05.05.20092494.
Soliman et al., "Derivation and Validation of a Novel Right-sided Heart Failure Model After Implantation of Continuous Flow Left Ventricular Assist Devices", Circulation, vol. 137, 2018, pp. 891-906, doi: 10.1161/CIRCULATIONAHA.117.030543.
Tran et al., "Learning Spatiotemporal Features With 3d Convolutional Networks", Proceedings of the IEEE International Conference on Computer Vision, 2015, pp. 4489-4497, doi: 10.1109/ICCV.2015.510.
Wang et al., "Action Recognition with Improved Trajectories", Proceedings of the 2013 IEEE International Conference on Computer Vision, 2013, pp. 3551-3558, doi: 10.1109/ICCV.2013.441.
Zhang et al., "Fully Automated Echocardiogram Interpretation in Clinical Practice", Circulation, vol. 138, 2018, pp. 1623-1635, doi: 10.1161/CIRCULATIONAHA.118.034338.

\* cited by examiner

| Layer name | Output size | 18-layer | 34-layer | 50-layer | 152-layer |
|---|---|---|---|---|---|
| conv1 | 112 × 112 | | 7 × 7 × 7, 64, stride 2 | | |
| conv2_x | 56 × 56 | | 3 × 3 × 3 max pool, stride 2 | | |
| | | $\begin{bmatrix} 3\times3\times3, & 64 \\ 3\times3\times3, & 64 \end{bmatrix} \times 2$ | $\begin{bmatrix} 3\times3\times3, & 64 \\ 3\times3\times3, & 64 \end{bmatrix} \times 3$ | $\begin{bmatrix} 1\times1\times1, & 64 \\ 3\times3\times3, & 64 \\ 1\times1\times1, & 256 \end{bmatrix} \times 3$ | $\begin{bmatrix} 1\times1\times1, & 64 \\ 3\times3\times3, & 64 \\ 1\times1\times1, & 256 \end{bmatrix} \times 3$ |
| conv3_x | 28 × 28 | $\begin{bmatrix} 3\times3\times3, & 128 \\ 3\times3\times3, & 128 \end{bmatrix} \times 2$ | $\begin{bmatrix} 3\times3\times3, & 128 \\ 3\times3\times3, & 128 \end{bmatrix} \times 4$ | $\begin{bmatrix} 1\times1\times1, & 128 \\ 3\times3\times3, & 128 \\ 1\times1\times1, & 512 \end{bmatrix} \times 4$ | $\begin{bmatrix} 1\times1\times1, & 128 \\ 3\times3\times3, & 128 \\ 1\times1\times1, & 512 \end{bmatrix} \times 8$ |
| conv4_x | 14 × 14 | $\begin{bmatrix} 3\times3\times3, & 256 \\ 3\times3\times3, & 256 \end{bmatrix} \times 2$ | $\begin{bmatrix} 3\times3\times3, & 256 \\ 3\times3\times3, & 256 \end{bmatrix} \times 6$ | $\begin{bmatrix} 1\times1\times1, & 256 \\ 3\times3\times3, & 256 \\ 1\times1\times1, & 1024 \end{bmatrix} \times 6$ | $\begin{bmatrix} 1\times1\times1, & 256 \\ 3\times3\times3, & 256 \\ 1\times1\times1, & 1024 \end{bmatrix} \times 36$ |
| conv5_x | 7 × 7 | $\begin{bmatrix} 3\times3\times3, & 512 \\ 3\times3\times3, & 512 \end{bmatrix} \times 2$ | $\begin{bmatrix} 3\times3\times3, & 512 \\ 3\times3\times3, & 512 \end{bmatrix} \times 3$ | $\begin{bmatrix} 1\times1\times1, & 512 \\ 3\times3\times3, & 512 \\ 1\times1\times1, & 2048 \end{bmatrix} \times 3$ | $\begin{bmatrix} 1\times1\times1, & 512 \\ 3\times3\times3, & 512 \\ 1\times1\times1, & 2048 \end{bmatrix} \times 3$ |
| | 1 × 1 | | Average Pool 3D, 10 Dense, Sigmoid | | |

SYSTEMS AND METHODS FOR PREDICTING POST-OPERATIVE RIGHT VENTRICULAR FAILURE USING ECHOCARDIOGRAMS

CROSS REFERENCE TO RELATED APPLICATIONS

The current application is a national stage of PCT Patent Application No. PCT/US2021/029168, entitled "Systems and Methods For Predicting Post-Operative Right Ventricular Failure Using Echocardiograms" to Aror et al., filed Apr. 26, 2021, which claims the benefit of U.S. Provisional Patent Application No. 63/018,270 entitled "Systems and Methods For Predicting Post operative Right Ventricular Failure Using Echocardiograms" to Aror et al., filed Apr. 30, 2020, the disclosures of which are incorporated herein by reference in their entirety.

FIELD OF THE INVENTION

The present invention generally relates to assessing cardiac function, and more specifically, to systems and methods incorporating machine learning to predict post-operative right ventricular failure using echocardiograms.

BACKGROUND

Heart failure affects more than 6.5 million people in the United States alone, with an estimated 960,000 new cases diagnosed each year. A heart transplant remains the gold standard for treating patients with end-stage heart failure. Demand, however, far outpaces the supply of transplantable hearts. Left ventricular assist devices (LVADs) offer a mechanical alternative to transplantation, and the number of patients supported by these battery-powered mechanical pumps have steadily grown since 2008. In the contemporary era, an estimated 3500 LVAD implants are performed each year, with 10-year outcomes comparable to transplants. Unfortunately, approximately a third of all patients implanted with LVADs, develop a clinically significant degree of right ventricular (RV) failure soon after the procedure. Severe RV failure remains the single largest contributor to short-term mortality in this patient population.

The standard for determining which patients receive advanced right ventricular support devices can be a clinical gestalt, involving the patients' clinical course, lab parameters, and a qualitative assessment of myocardial function using a transthoracic echocardiogram—a ubiquitous and cost-effective ultrasound video of the heart.

SUMMARY OF THE INVENTION

Systems and methods incorporating machine learning to predict post-operative right ventricular failure using echocardiograms are described. An embodiment of the invention includes a system for predicting post-operative right ventricular (RV) failure that includes: a processor; a memory containing an automated echocardiography application, where the automated echocardiography application directs the processor to: obtain echocardiography video data describing a patient's heart; generate a plurality of dense trajectory descriptors based on the echocardiography video data; reduce the plurality of dense trajectory descriptors to a bag-of-words representation; generate, using an unsupervised neural network, a first prediction metric of RV failure based on the bag-of-words representation; generate, using a supervised neural network, a second prediction metric based on the echocardiography video data; generate an output prediction metric by applying a weighted classifier to the first prediction metric and the second prediction metric.

In a further embodiment, a neural network is a 3-dimensional convolutional neural network.

In a further embodiment, the 3-dimensional convolutional network comprises a plurality of convolutional layers, a plurality of max-pooling layers, and a plurality of connected layers.

In a further embodiment, the convolutional layers utilize a 3×3×3 kernel and the first convolutional layer does not convolve over a temporal dimension.

In a further embodiment, the system further processes two parallel spatiotemporal streams of data from the echocardiography videos, wherein a greyscale video channel and an optical flow stream are combined with a convolutional neural network.

In a further embodiment, the plurality of dense trajectory descriptors describes shape, appearance, and motion for a plurality of feature points within the echocardiography video data.

In a further embodiment, to reduce the plurality of dense trajectory descriptors, the automated echocardiography application further directs the processor to apply an unsupervised k-means clustering model.

In a further embodiment, to generate the first prediction metric, the automated echocardiography application further directs the processor to apply a Gaussian process classifier to the bag-of-words representation.

In a further embodiment, the system generates a probabilistic predication of RV failure outcome using the Gaussian process classifier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

DETAILED DESCRIPTION OF THE DRAWINGS

Turning now to the drawings, systems and methods for predicting post-operative right ventricular failure using echocardiograms analyzed with machine learning in accordance with various embodiments of the invention are illustrated. In many embodiments, the systems and methods can be generalizable to any health related and/or cardiac clinical decision support application where treatment or patient selection is guided by qualitative health imaging and/or video assessments. In many embodiments, the assessments can be based on echocardiography image and video data. In many embodiments, the machine learning system can analyze raw image and/or video data to generate predictive probabilities of post-operative adverse events.

Many embodiments provide for an echocardiography machine learning (ML) system that enables time resolved characterization of motion parameters from echocardiograms. Many embodiments use the ML system to predict post-operative RV failure in LVAD patients, using pre-operative echocardiograms. Many embodiments of the ML system can use any combination of video data and/or other types of data, such as age, BMI, and other demographic information for predictions. Accordingly, the prediction capabilities of the ML system in accordance with many embodiments outperforms many of the prior human conducted scoring methods that evaluate RV failure risk including those of contemporary RV failure risk scores, and furthermore the ML system can outperform heart failure echocardiography experts in independent clinical evaluation.

In particular, artificial intelligence has enabled automated systems to meet or exceed the performance of clinical experts across a range of image analysis tasks, from detection and diagnosis of disease to prediction of disease progression. However, these systems typically draw conclusions from static images, which may not be sufficient for many types of diseases, including assessment of RV failure risk. Accordingly, many embodiments of the ML system may use a video based AI system that processes one or more spatiotemporal streams of data from echocardiography videos. In many embodiments, other types of data, such as patient health data (e.g., age, BMI, among others) can be used as a fusion model alongside the video data for predictions.

In many embodiments, the ML system may process several spatiotemporal streams of data from echocardiography videos. In many embodiments, the ML system may process two parallel spatiotemporal streams of data from echocardiography videos. In many embodiments, a grey-scale video channel and an optical flow streams can be combined within a convolutional neural network architecture with concatenation of activations prior to a terminal fully connected layer. Many embodiments may use different machine learning techniques, including different pretraining strategies, optimizers, input streams, and model architectures as appropriate to the requirements of specific applications in order to perform the predictions and risk assessment. Many embodiments may use a 3-dimensional 152-layer residual network for the echocardiography ML system. Architectural details of the ML system and training strategies in accordance with many embodiments are described in detail below.

In many embodiments, a radiomics method for an echocardiography AI system can be utilized to extract hundreds of thousands of motion parameters per ECHO. In various embodiments, the AI system can be utilized for the prediction of post-operative RV failure in LVAD patients by using pre-operative ECHOs. In many embodiments, systems and methods for predicting post-operative right ventricular failure using echocardiograms can be utilized to randomize patients at high risk of developing post-op RV failure to various right ventricular rescue trials that evaluate the efficacy of right ventricular treatment options by integrating AI systems within pre-operative clinical workflows. In several embodiments, the integrated AI systems can serve as a clinical decision support system for instituting effective RV rescue treatments. In certain embodiments, systems and methods for predicting post-operative right ventricular failure using echocardiograms can be utilized in early detection of heart failure, disease phenotyping, and a multitude of cardiac clinical decision support applications where treatment is guided by qualitative echocardiography assessments. While specific systems and methods for predicting post-operative right ventricular failure using echocardiograms are described, any of a variety of systems and methods for predicting post-operative right ventricular failure using echocardiograms can be utilized in accordance with various embodiments of the invention. Methods for predicting post-operative right ventricular failure using echocardiograms are described.

Methods for Predicting Post-operative RV Failure Using Echocardiograms

Machine Learning Pipeline

Figure 1:
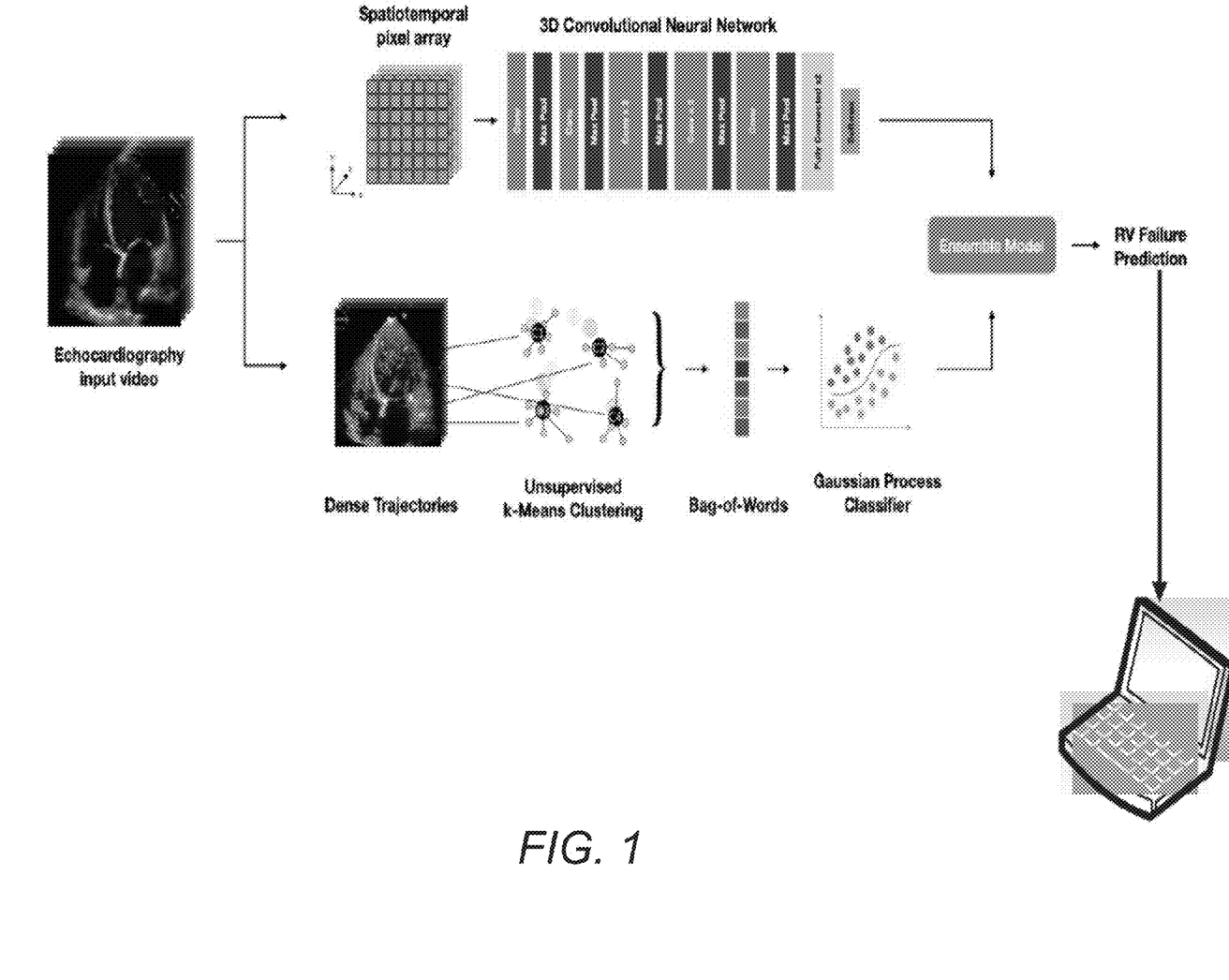
FIG. 1 illustrates a diagram of an artificial intelligence (AI) echocardiography pipeline where an input can be an apical 4 chamber transthoracic echocardiogram (ECHO), which can be processed by two parallel processes and where a final prediction of RV failure can be made by combining the predictions from each of the two parallel processes in accordance with an embodiment of the invention.

In many embodiments, the ML system can use an automated echocardiography analysis pipeline that can be a combination of two processes, as illustrated in FIG. 1 in accordance with an embodiment of the invention. In many embodiments, a first process can be a dense trajectory process that tracks motion features across short time intervals. A second process can be a 3-d convolutional neural network which can be built (but not limited to) by using the Keras Framework (an open source neural network library written in Python) with a TensorFlow (Google; Mountain View, CA, USA) backend and Python, that can track motion features and structural features over multiple cardiac cycles. A number of trajectory descriptors (e.g., six trajectory descriptors) representing information of shape, appearance, and motion can be calculated for each tracked feature point. The totality of local spatiotemporal information can be reduced to a bag-of-words representation using an unsupervised k-means clustering method, which can produce a probabilistic prediction of RV failure outcome by utilizing a supervised Gaussian Process Classifier. While specific clustering methods and classifiers are described above, any of a variety of clustering methods and classifiers can be utilized in accordance with various embodiments of the invention.

In many embodiments, the 3-d convolutional neural network can include a number of convolutional layers, max-pooling layers, and fully connected layers that can culminate into a normalized probability distribution classifier for RV failure prediction. In certain embodiments, the 3-d convolutional neural network can include 8 convolutional layers, 5 max-pooling layers, and 2-fully connected layers that can culminate into a normalized probability distribution (softmax) classifier for RV failure prediction, as illustrated in FIG. 1 in accordance with an embodiment of the invention. Note that the specific number of convolutional layers, max-pooling layers and connected layers can vary. As illustrated in FIG. 1, the convolutional layers can utilize a 3×3×3 kernel, except for the first convolutional layer which does not convolve over a temporal dimension. Note that the specific number of kernels can vary. The network weights can be initialized using a normal initializing scheme, and can be optimized using an optimization algorithm. The network can be trained for 25 epochs on a batch size of 8, with an initial learning rate of $1 \times 10^{-5}$. Note that the specific number of epochs, batch sizes and learning rates can vary. Training can be stopped early if the loss does not improve for 5 epochs. For each echocardiogram, 5 random 64-frame clips of the full movie can be subsampled and passed through the trained neural network. The average of the 5 outputs can be calculated to predict RV failure. The predicted probabilities of RV failure from both the dense trajectory analysis and convolutional neural network can be ensembled using a weighted soft-voting classifier. In the illustrated embodiment, the probabilities for each outcome class can be calculated for two halves of the AI system, and an empirically derived weight can be applied to each probability and then summed together. The outcome class with the highest weighted sum can be outputted as the predicted label. The models can be trained on servers. In several embodiments, the models can be trained on servers. While specific machine learning pipelines are described above, any of a variety of machine learning pipelines can be utilized in accordance with various embodiments of the invention. Data sources and study population are disclosed further below.

Figure 3:
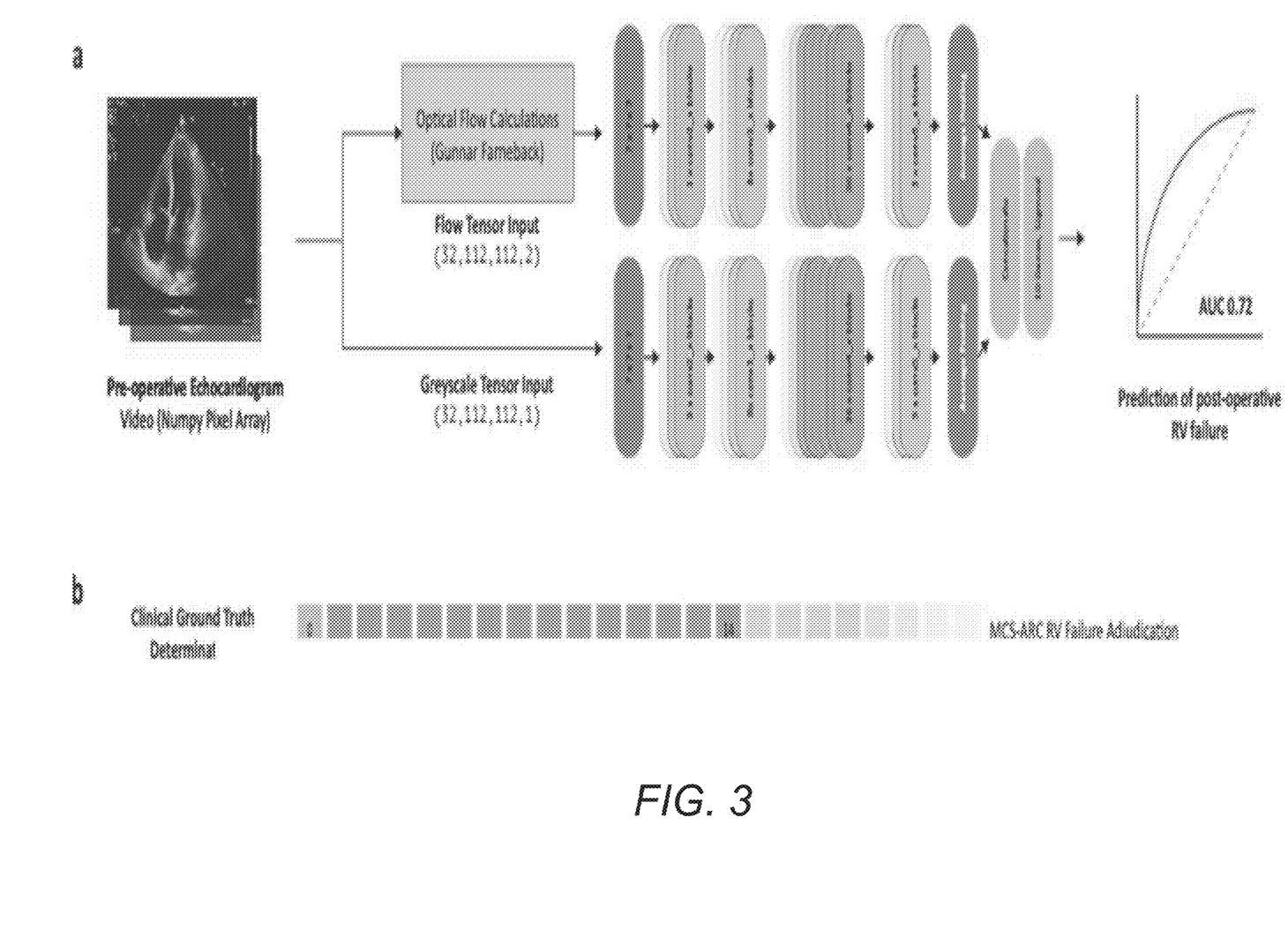
FIG. 3 illustrates a machine learning system with pre-operative echocardiography videos processed as a stack of frames in accordance with an embodiment of the invention.

In many embodiments, a machine learning system can be trained on echocardiography videos stacked as a number of frames. FIG. 3 illustrates a machine learning system with pre-operative echocardiography videos processed as a stack of 32 frames. As illustrated in FIG. 3, a two-stream implementation of raw greyscale videos and optical flow channels are fed into a 3D convolutional neural network to produce the prediction of RV failure. FIG. 3 also illustrates the clinical ground truth can be determined largely by the persistent need for inotropes past post-operative day 14 or right ventricular mechanical circulatory assist devices during the post-operative recovery period. Although FIG. 3 illustrates a particular machine learning system with a 3D convolutional neural network, any of a variety of process and machine learning techniques may be utilized as appropriate to the requirements of specific applications in accordance with embodiments of the invention.

Figure 2A:
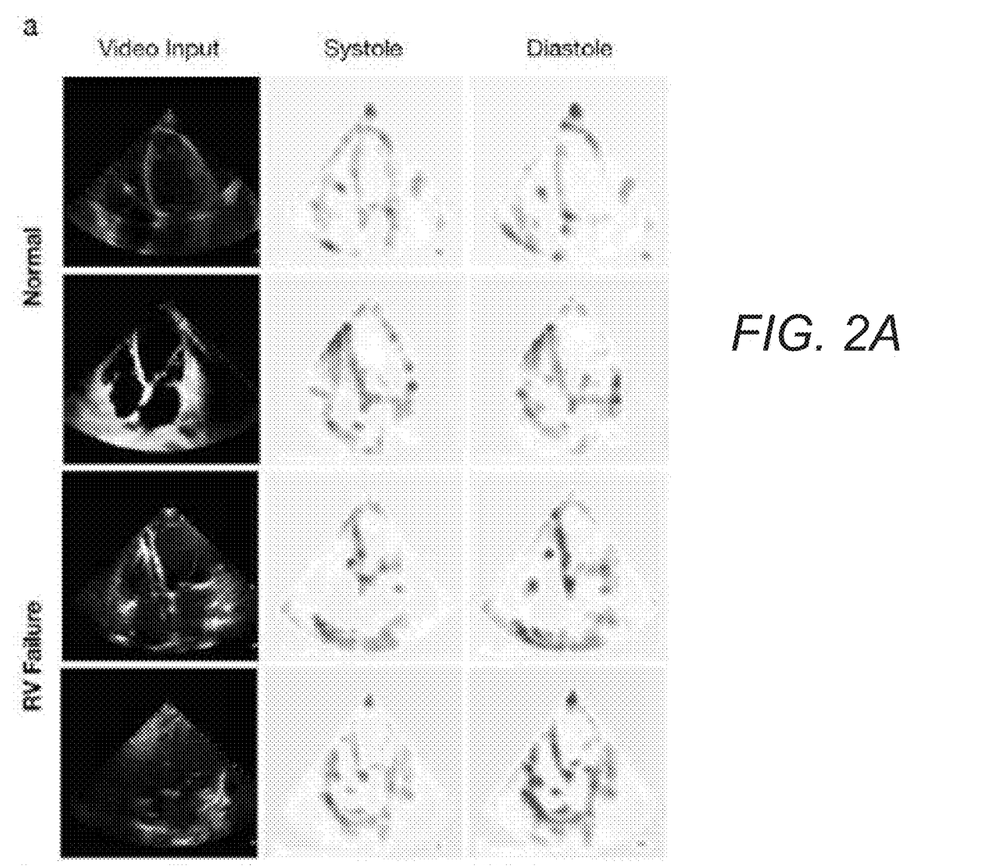
FIG. 2A shows representative input echocardiograms for a 3d-convolutional neural network, and layer-wise relevance propagation (LRP) visualizations for both systolic and diastolic phases of the cardiac cycle across patients with and without RV failure.
Figure 2B:
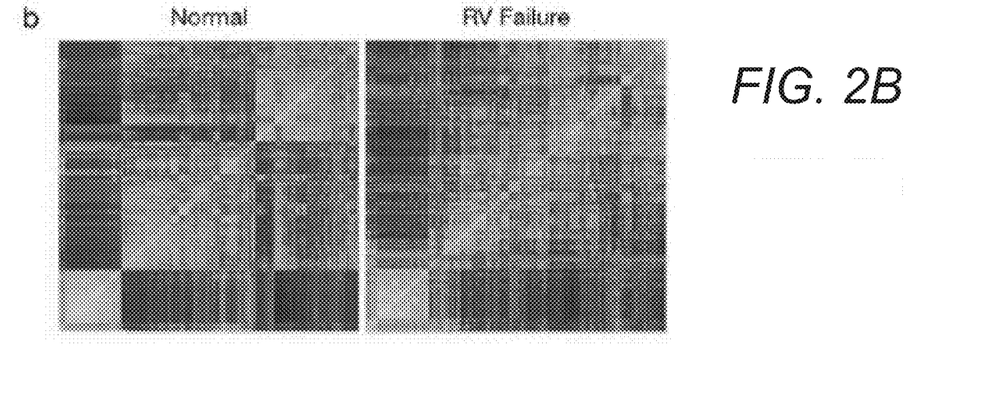
FIG. 2B shows heatmaps generated for the trajectory descriptor from a dense trajectory pipeline, visualizing the subtle motion features tracked in normal vs RV failure cases.

In several embodiments, layer-wise relevance propagation (LRP) visualizations can show that for each patient regions of activation for the 3-d convolutional neural network can be localized exclusively to the myocardium and valves. The cardiac chambers themselves may not show activation. Furthermore, motion characteristics of different regions of the heart an contribute towards the prediction of RV failure at different phases of the cardiac cycle as shown in FIGS. 2A and 2B. In particular, FIG. 2A illustrates representative input ECHOs for the 3d-convolutional neural network, and LRP visualizations for both systolic and diastolic phases of the cardiac cycle across patients with and without RV failure. FIG. 2B shows heatmaps generated for a trajectory descriptor from the dense trajectory pipeline, visualizing the subtle motion features tracked in normal vs RV failure cases. While specific visualizations are described above, any of a variety of different visualizations can be utilized in accordance with various embodiments of the invention. Discussion and analysis are disclosed further below.

In several embodiments, an AI echocardiography system can be utilized which is capable of extracting subtle myocardial motion aberrations for downstream clinical analyses. In many embodiments, the AI system can be used to predict an outcome of post-operative RV failure in patients considered for LVAD implant. In many embodiments, the AI echocardiography system can outperform board certified clinicians equipped with both manually extracted echo metrics and state of the art clinical risk scores.

In certain embodiments, the AI system can extract spatiotemporal information from cardiac musculature and valves by default—the principle regions of interest in cardiac diseases. In various embodiments, methods can characterize subtle regional aberrations in myocardial motion for downstream analyses, in ways that traditional manually extracted echocardiographic measures may fail to capture.

In several embodiments, systems and methods for predicting post-operative right ventricular failure using echocardiograms can track features of importance with no additional human supervision in the form of outlines or labels. In many embodiments, systems and methods for predicting post-operative right ventricular failure using echocardiograms can enable rapid deployment of methods to a diverse array of echocardiography-based problems, in an unbiased, and structure agnostic fashion. In certain embodiments, systems and methods for predicting post-operative right ventricular failure using echocardiograms can predict a binary outcome of RV failure, and can be utilized to predict either continuous or multi-class outcomes of interest. While specific systems and methods for predicting post-operative right ventricular failure using echocardiograms are described, any of a variety of different systems and methods for predicting post-operative right ventricular failure using echocardiograms can be utilized in accordance with various embodiments of the invention.

In many embodiments, primary outcome of RV failure can be dichotomized in order to include only severe or greater grades of RV failure. This can be based on significantly higher risk of mortality in these patients compared to those with moderate and lower grades of disease. In several embodiments, analysis using the AI pipeline trained on data with moderate or greater grades of RV failure can be repeated.

In certain embodiments, the analysis of ECHOs rather than using clinical surrogate parameters can be that it allows for a direct assessment of the heart. In many embodiments, the AI echocardiography systems tools can be utilized as a clinical decision support system for instituting effective RV rescue treatments in patient populations. In various embodiments, systems and methods for predicting post-operative right ventricular failure using echocardiograms can be used in early detection of heart failure, disease phenotyping, and a multitude of cardiac clinical decision support applications where treatment is guided by qualitative echocardiography assessments.

Saliency Maps and Visualizations

Figure 4:
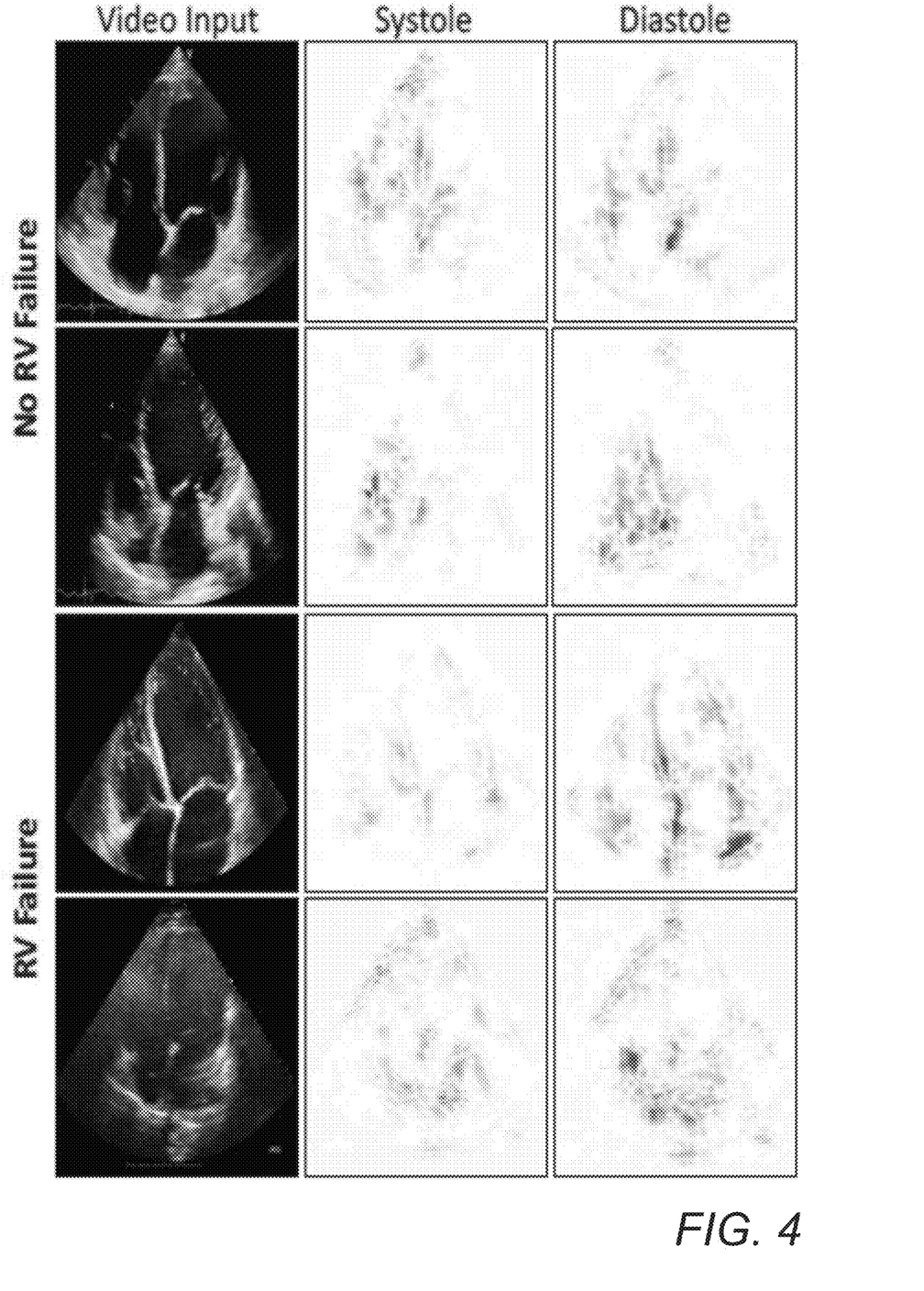
FIG. 4 illustrates saliency maps for pre-operative echocardiograms with representative input videos and visualizations for both systolic and diastolic phases of the cardiac cycle across patients with and without RV failure in accordance with an embodiment of the invention.

Interpretability of clinical AI systems has implications in identifying failure modes as well as in establishing trust and confidence in end-users. Accordingly, many embodiments may utilized gradient backpropagation to generate saliency maps. FIG. 4 illustrates saliency maps for pre-operative echocardiograms with representative input videos and visualizations for both systolic and diastolic phases of the cardiac cycle across patients with and without RV failure in accordance with an embodiment of the invention.

In many embodiments, saliency maps can be computed based on the imputed gradient of the target output with respect to input, where non-negative gradients are back-propagated. In particular, the goal of this technique is to find input data that would exemplify the features the network uses to predict RV Failure (or lack thereof). Accordingly, for each patient, regions of activation can be localized exclusively to the myocardium and valves. The cardiac chambers (ventricles and atria) themselves may show no activation. Furthermore, motion characteristics of specific regions of the heart can contribute towards the prediction of RV failure at different phases of the cardiac cycle, as illustrated in FIG. 2. In patients where the AI system in accordance with an embodiment of the invention can correctly predicted RV failure, saliency maps can be localized over the interventricular septum, right atrium, and the region of the tricuspid annulus.

Accordingly, many embodiments of the machine learning system are capable of characterizing subtle myocardial motion aberrations on echocardiography for downstream clinical analyses. Many embodiments of the ML system can predict a binary outcome of RV failure. Certain embodiments of the ML system can readily be extended to predict continuous and multi-class outcomes of interest.

Many embodiments of the AI system can directly analyze spatiotemporal information from the cardiac musculature and valves, the principal regions of interest in cardiac diseases. Accordingly, this enables the AI system and algorithm to characterize subtle, regional aberrations in myocardial motion, that traditional manually extracted echocardiographic measures fail to capture.

Many embodiments of the ML system track features of importance without human supervision in the form of segmentation masks. This method may not be dependent on cardiac view plane or chamber, enabling rapid deployment of the ML system to a diverse array of echocardiography problems. The ML system can use two streams of spatiotemporal information in the form of greyscale video channels and optical flow to directly predict downstream outcomes of interest. Combined two-stream networks can achieve state-of-the-art performance on large video recognition datasets. The ML system can make inferences on a single study within 500 ms on a single Nvidia GeForce RTX 2080Ti GPU. An additional computational overhead of 10 s however may be needed for calculating optical flow per input video. Accordingly, the ML system can integrate faster deep learning methods of optical flow estimation within the AI pipeline for applications that use real time inference.

Data Pre-Processing:

In many embodiments, echocardiograms can be first de-identified by stripping all private health information (PHI) from file metadata and by obscuring any sensitive information in the videos. Areas outside of the scanning sector can be masked to remove miscellaneous markings in the video frames that may otherwise influence the neural networks. The videos cab then be normalized by dividing each pixel value by the pixel of maximal intensity. The frames of the processed videos can additionally down-sampled by bi-linear interpolation to a particular resolution (e.g., 112×112 resolution) for training and evaluation. In many embodiments, optical flow can be calculated prior to model training using an OpenCV implementation of the Gunnar Farnebäck method based on polynomial expansion. In many embodiments, additional data augmentation operations such as random 3-dimensional shearing, scaling, rotation, brightness multiplication can be utilized as part of the training loop.

Figure 5A:
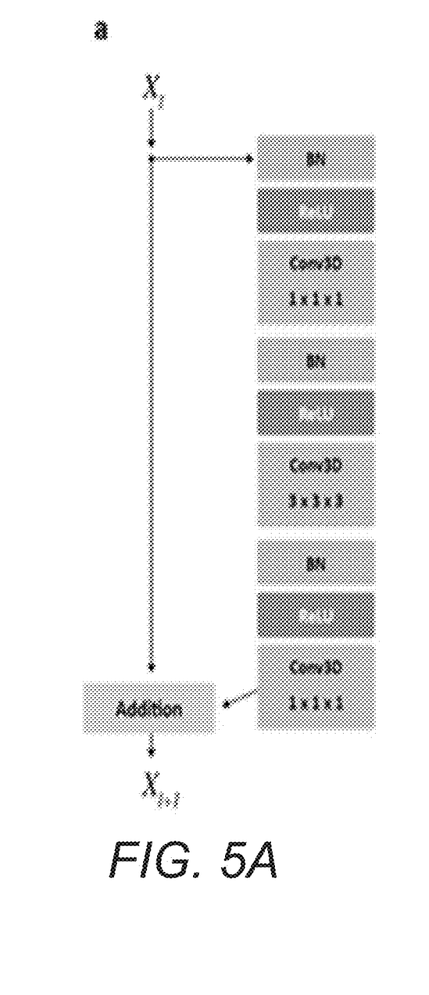
FIG. 5A illustrates using a two-stream fusion 152-layer 3D Residual Network with bottlenecks incorporated within the residual blocks in accordance with an embodiment of the invention.
Figure 5B:
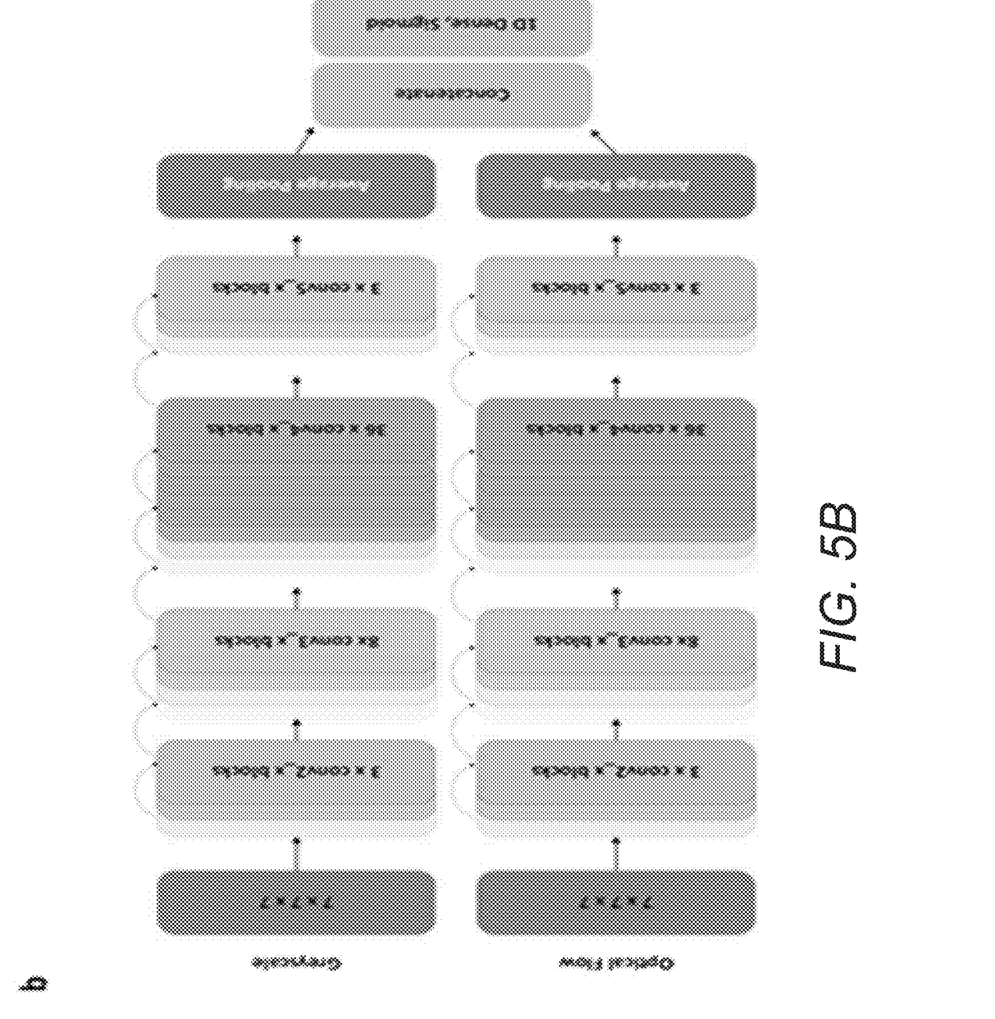
FIG. 5B illustrates an overall architecture of a two-stream network with parallel greyscale and optical flow 152-layer residual networks, converging to a single concatenation layer past each terminal average pooling layer in accordance with an embodiment of the invention.

Neural Network Architecture and Training:

As discussed, many embodiments can use a 3-dimensional convolutional neural network, built using the Keras Framework with a TensorFlow 2.0 (Google; Mountain View, CA, USA) backend and Python, that tracks motion features and structural features in blocks of 32 consecutive frames. Many embodiments of the ML system can use bottlenecked residual blocks expanded to 3-dimensions. Many embodiments can use a two-stream fusion 152-layer 3D Residual Network with bottlenecks incorporated within the residual blocks as illustrated in FIG. 5 in accordance with an embodiment of the invention. Note that any number of layers, input streams, bottleneck residual blocks and/or neural network architectures that allow for skip connections between layers can be utilized as appropriate for the requirements of specific applications in accordance with embodiments of the invention.

As illustrated in FIG. 5A, the Residual Network blocks may allow for skip connections between different layers. The bottleneck residual units may contain in sequence: Batch Normalization, ReLU Activation, Conv3D, Batch Normalization, ReLU Activation, and then a final Conv3D layer. The output can be combined with a skip connection via an Addition Layer. Each 3D Convolutional layer can be additionally set with channel groups=1, and dilation rate set to 1. FIG. 5b illustrates an overall architecture of a two-stream network with parallel greyscale and optical flow 152-layer residual networks, converging to a single concatenation layer past each terminal average pooling layer in accordance with an embodiment of the invention. Although FIG. 5 illustrates a particular architecture of machine learning using a parallel greyscale and optical flow process, any of a variety of processes may be utilized as appropriate to the requirements of specific applications in accordance with embodiments of the invention.

Figure 6:
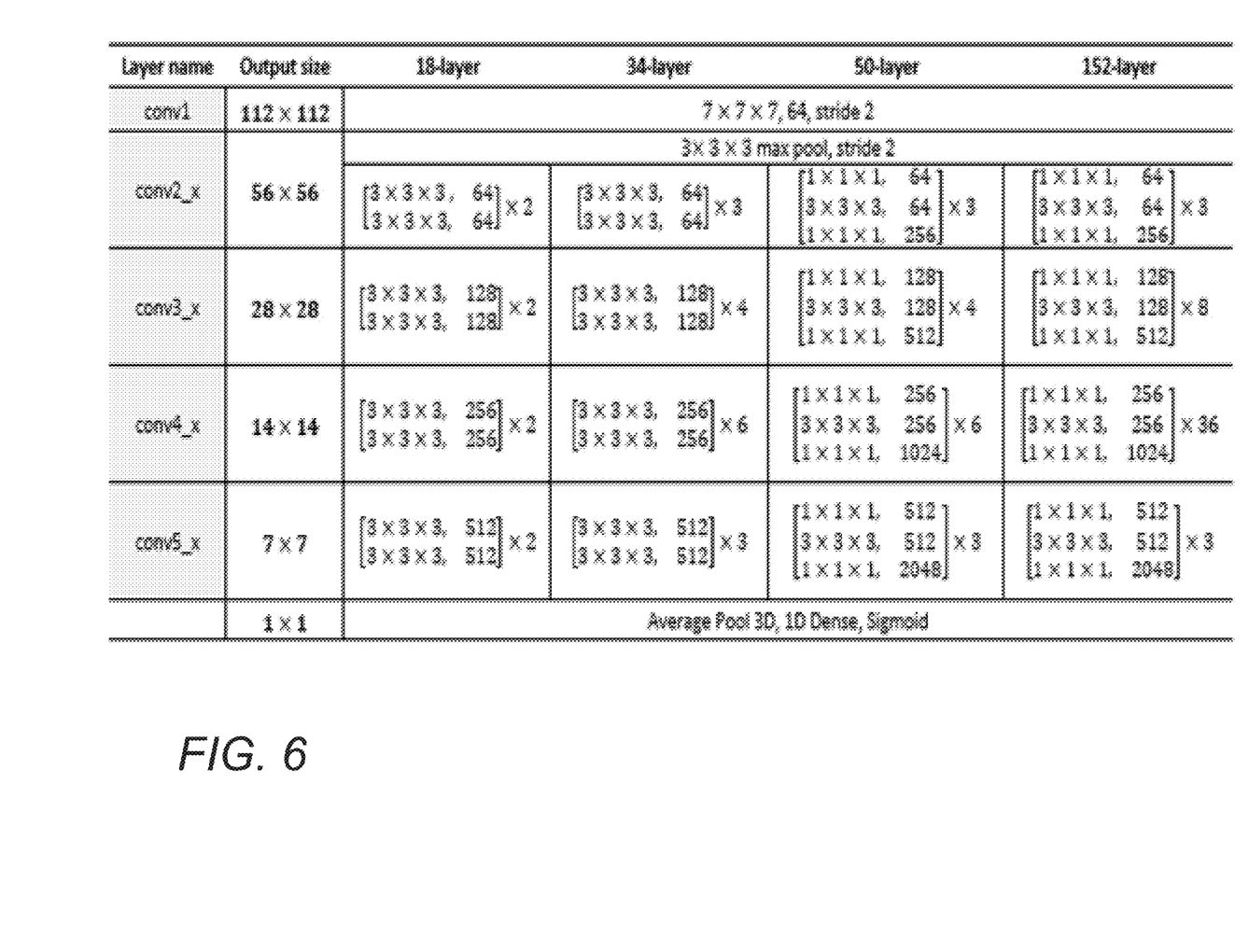
FIG. 6 illustrates an initial convolutional layer that has a 7×7×7 receptive field with a kernel size of 64 and stride of 2 in accordance with an embodiment of the invention.

FIG. 6 illustrates an initial convolutional layer that has a 7×7×7 receptive field with a kernel size of 64 and stride of 2. L2 regularization of 1e-4 can be used for each residual block. The different 3D ResNet depths may contain varying numbers of convolutional layers for sizes 56×56 down to 7×7. The smaller 18 and 34-layer ResNets can employ residual blocks without 1×1×1 bottlenecks. Although FIG. 6 illustrates a particular receptive field, kernel size and stride, any of a variety of values may be utilized as appropriate to the requirements of specific applications in accordance with embodiments of the invention.

In many embodiments, the residual blocks utilize a convolutional layer with a 3×3×3 kernel, sandwiched between two 1×1×1 convolutional layers. The first convolutional layer can utilize a 7×7×7 kernel. In many embodiments, the network weights can be initialized using a normal initializing scheme and optimized. In many embodiments, the network can be trained for a number of epochs (e.g., 50 epochs) on a particular batch size (e.g., batch size of 8), with an initial learning rate of $1\times10^{-5}$. Training can be stopped early if the training loss does not improve for a number of epochs (e.g., 5 epochs). For each echocardiogram, a number of random fame clips (e.g., 5 random 32-frame clips) of the full movie can be subsampled and passed through the trained neural network. The average of the outputs can be calculated to predict RV failure. In many embodiments, hyper parameter tuning can be carried out on the validation dataset. Many embodiments of the ML system can implement a proportional loss weighting strategy during training with a binary cross-entropy loss function, to account for the effect of minor class imbalance. The binary cross-entropy loss function is given by the following equation:

$$H(y, \hat{y}) = -\frac{1}{N} \sum_{k=1}^{N} [y_i \log \hat{y}_r + (1 - y_i) \log(1 - \hat{y}_r)]$$

Pretraining

In many embodiments, candidate networks can be pretrained on a dataset (e.g., the Kinetics-600 dataset) for video action recognition. Videos in the dataset can be converted to greyscale and optical flow and subsampled for a number (e.g., 32) of consecutive frames prior to pre-training. Pretraining on the dataset can be performed on servers. The dataset initialized networks can then be trained on an echocardiography dataset (e.g., Stanford AI in Medicine Center echocardiography dataset) for Ejection Fraction prediction on Apical 4-Chamber echocardiography videos (e.g., with over 10,000 Apical 4-Chamber echocardiography videos). Training can be stopped when validation loss does not improve, and the model weights can be saved. In many embodiments, the networks for RV failure prediction can be initialized with these weights and the terminal linear activation function can be replaced by a sigmoid function. In many embodiments, pretraining can improve training convergence, with higher validation AUC and lower cross-entropy losses.

Visualizations and Interpretations

Many embodiments of the ML system may use gradient backpropagation to generate saliency maps for the AI system as it makes predictions of RV failure outcome when passed through the 3-dimensional convolutional neural network.

Visualization of representation learned by higher layers of the network can be generated by propagating the output activation back through the ReLU function in each layer l and setting the negative gradients to zero:

$$R_i^{(l)} = (f_i^l > 0) \cdot (R_i^{l+1} > 0) \cdot R_i^{l+1}$$

Certain embodiments of the ML system may use different visualization techniques such as layer wise relevance propagation. In many embodiments, the neurons that contribute the most to the higher layers receive the most 'relevance' from it. The relative contribution of each pixel towards the final predicted value can be quantified to satisfy the following equation:

$$R_{i \leftarrow k}^{(l,l+1)} = R_k^{(l+1)} \frac{a_i w_{ik}}{\sum_h a_h w_{hk}}$$

The total relevance R is conserved between layers l. During each forward pass, neuron i inputs $a_i w_{ik}$ to the next connected neuron k. The messages $R_{i \leftarrow k}^{(l,l+1)}$ distribute the relevance $R_k^{(l+1)}$ of a neuron k, onto the preceding neurons that feed into it at layer l. The presence of skip connections in 3D residual networks violates the assumptions of relevance conservation, limiting us to Gradient backpropagation.

AI Performance:

In many embodiments, the dataset can be split in an approximate 66:17:17 ratio into a training, validation, and test dataset. The stratified split can ensure a proportional numbers of unique patients with and without RV failure in each group. The validation set can be used for hyper parameter tuning and an ensemble of different models (e.g., 3 models) trained with identical settings can be used to generate final predictions at the scan level. On freezing the model weights, model performance can be evaluated on the testing dataset using the area under curve (AUC) of the receiver-operator characteristic and AUC of the precision-recall curve. As noted, the predictive performance of many embodiments of the ML system have been compared against clinicians equipped with two contemporary risk scores used in for predicting post-operative RV failure—the CRITT score and Penn score.

Figure 7:
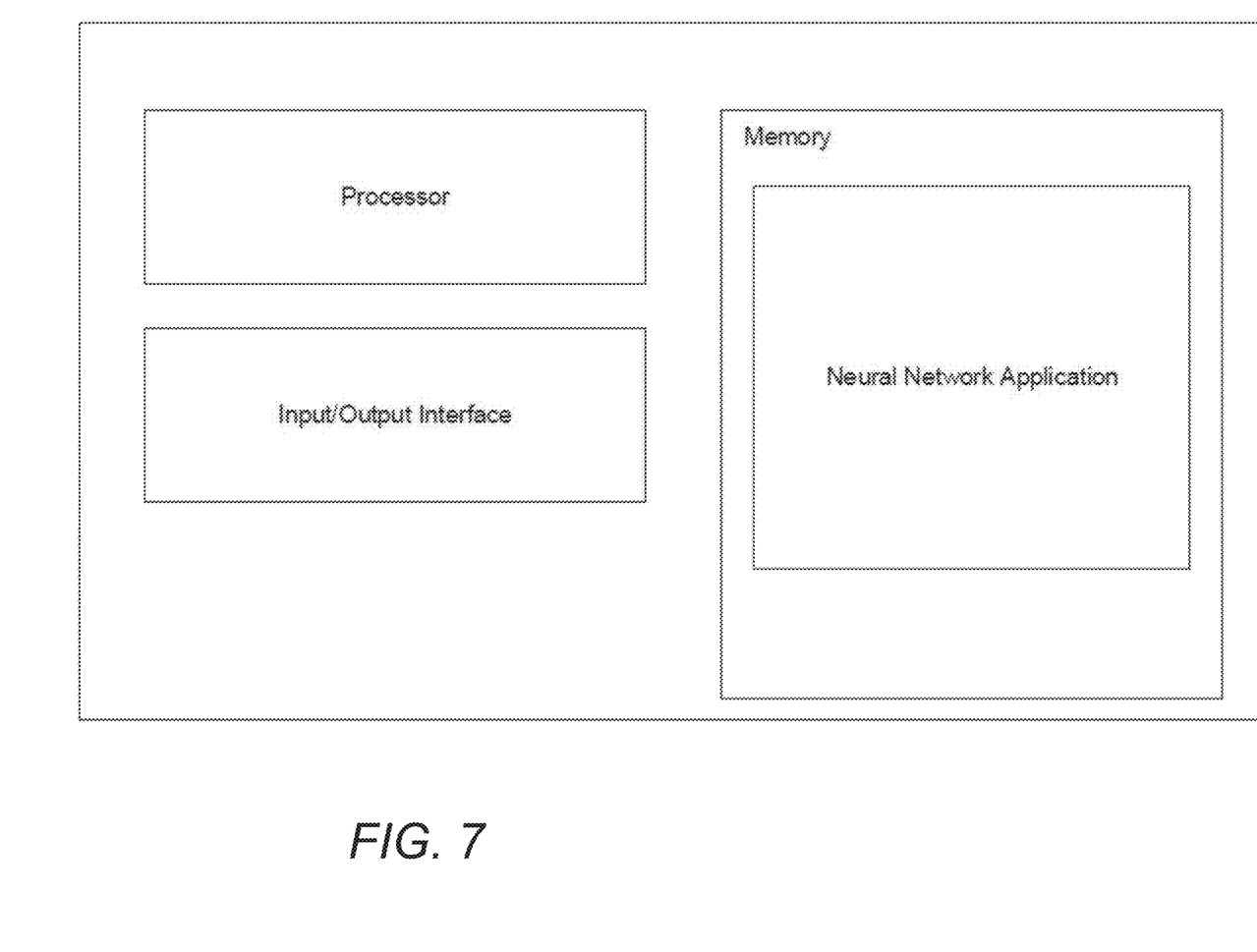
FIG. 7 provides a block diagram of a system for implementing a neural network application in accordance with an embodiment of the invention.

In many embodiments systems and methods for predicting post-operative right ventricular failure using echocardiograms include a processor and a memory containing an application for training a neural network, as illustrated in FIG. 7.

While the above descriptions and associated figures have depicted systems and methods for predicting post-operative right ventricular failure using echocardiograms, it should be clear that any of a variety of configurations for systems and methods for predicting post-operative right ventricular failure using echocardiograms can be implemented in accordance with embodiments of the invention. More generally, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A system for predicting post-operative right ventricular (RV) failure, the system comprising:
   a processor;
   a memory containing an automated echocardiography application, where the automated echocardiography application directs the processor to:
   obtain echocardiography video data describing a patient's heart;
   generate a plurality of dense trajectory descriptors based on the echocardiography video data;
   reduce the plurality of dense trajectory descriptors to a bag-of-words representation;
   generate, using an unsupervised neural network, a first prediction metric of RV failure based on the bag-of-words representation;
   generate, using a supervised neural network, a second prediction metric based on the echocardiography video data;
   generate an output prediction metric by applying a weighted classifier to the first prediction metric and the second prediction metric.

2. The system of claim 1, wherein a neural network is a 3-dimensional convolutional neural network.

3. The system of claim 2, wherein the 3-dimensional convolutional network comprises a plurality of convolutional layers, a plurality of max-pooling layers, and a plurality of connected layers.

4. The system of claim 2, wherein the convolutional layers utilize a 3×3×3 kernel and the first convolutional layer does not convolve over a temporal dimension.

5. The system of claim 1, further comprising processing two parallel spatiotemporal streams of data from the echocardiography videos, wherein a greyscale video channel and an optical flow stream are combined with a convolutional neural network.

6. The system of claim 1, wherein the plurality of dense trajectory descriptors describes shape, appearance, and motion for a plurality of feature points within the echocardiography video data.

7. The system of claim 1, wherein to reduce the plurality of dense trajectory descriptors, the automated echocardiography application further directs the processor to apply an unsupervised k-means clustering model.

8. The system of claim 1, wherein to generate the first prediction metric, the automated echocardiography application further directs the processor to apply a Gaussian process classifier to the bag-of-words representation.

9. The system of claim 8, further comprising generating a probabilistic predication of RV failure outcome using the Gaussian process classifier.

10. The system of claim 1, wherein the neural network is trained using a proportional loss weighting with a binary cross-entropy loss function given by:

$$H(y, \hat{y}) = -\frac{1}{N}\sum_{i=1}^{N}[y_i \log \hat{y}_i + (1-y_i)\log(1-\hat{y}_i)]$$

11. The system of claim 1, further comprising using gradient backpropagation to generate saliency maps for the system as it makes predictions of RV failure outcome when passed through the neural network.

12. The system of claim 1, further comprising generating visualization of representations learned by higher layers of the neural network by propagating an output activation back through a rectified linear unit (ReLU) function in each layer/and setting the negative gradients to zero:

$$R_i^{(l)} = (f_i^l > 0) \cdot (R_i^{l+1} > 0) \cdot R_i^{l+1}.$$

\* \* \* \* \*